United States Patent [19]

Layton

[11] 4,100,802
[45] Jul. 18, 1978

[54] LIQUID MEASURING DEVICE
[75] Inventor: Terry N. Layton, Wheeling, Ill.
[73] Assignee: The Kendall Company, Boston, Mass.
[21] Appl. No.: 804,653
[22] Filed: Jun. 8, 1977
[51] Int. Cl.² ............................................. G01F 1/02
[52] U.S. Cl. .................................... 73/215; 128/2 F; 128/2 F
[58] Field of Search .............. 73/421 R, 194 R, 215, 73/219, 223

[56] References Cited
U.S. PATENT DOCUMENTS

| 3,831,446 | 8/1974 | Dye | 128/2 F |
| 3,859,854 | 1/1975 | Dye | 73/215 |
| 3,871,230 | 3/1975 | Dye | 128/2 F |
| 3,871,231 | 3/1975 | Ciarico | 128/2 F |
| 3,982,898 | 9/1976 | McDonald | 128/2 F |

Primary Examiner—S. Clement Swisher
Attorney, Agent, or Firm—Powell L. Sprunger

[57] ABSTRACT

A device for measuring a liquid discharge comprising, a hollow receptacle having an inlet port adjacent an upper end of the receptacle to receive the liquid discharge. The device diverts and collects at least a portion of the discharge in order to determine the time duration of the discharge.

14 Claims, 7 Drawing Figures

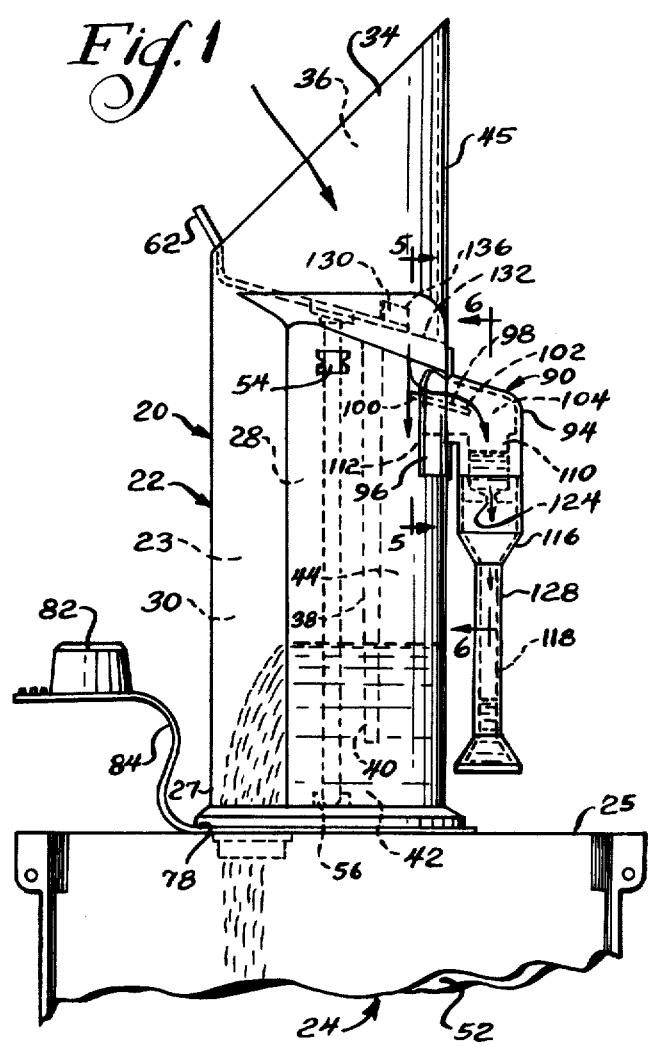
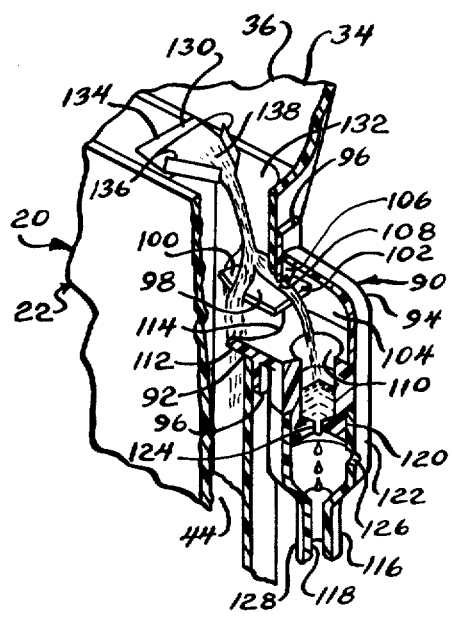
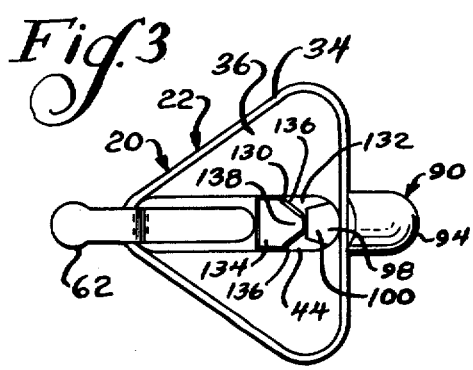
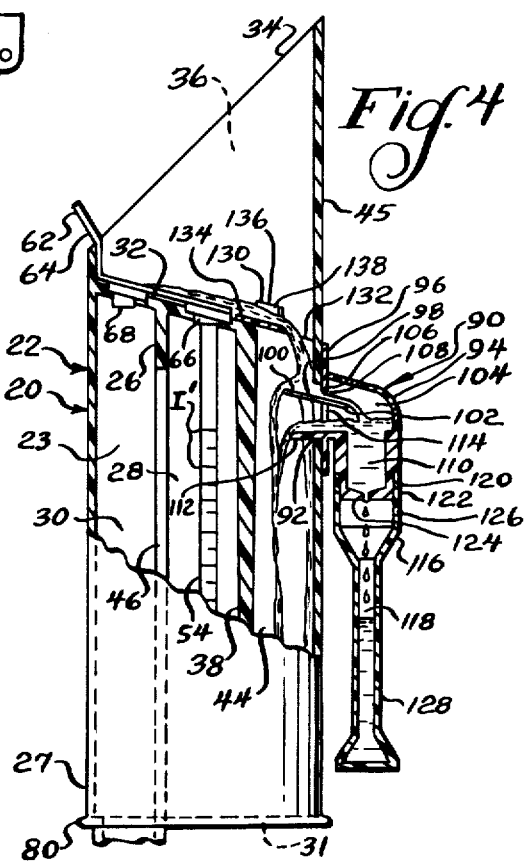

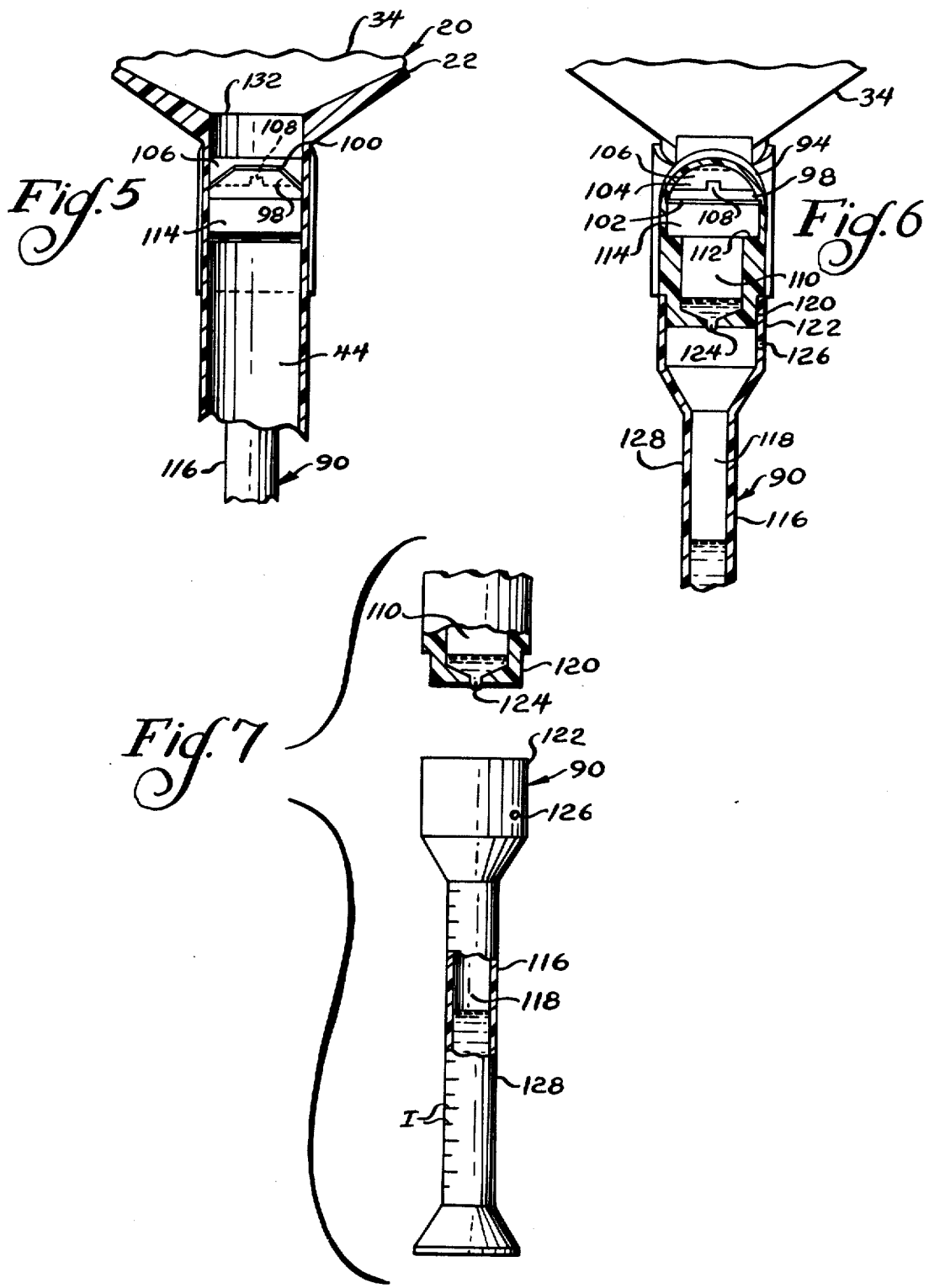

LIQUID MEASURING DEVICE

BACKGROUND OF THE INVENTION

The present invention relates to a device for measuring a discharge of liquid.

In the past, it has been found desirable to obtain various data pertaining to a liquid discharge. In particular, it was discovered that many urological problems could be readily diagnosed by analyzing information obtained during the natural voiding of urine by patients. Presently, various types of devices are utilized to obtain data on the urine stream, such as total volume, average flow rate, force, velocity, and configuration of the stream.

Most of these devices have suffered from less than total reliability because they have required the presence of one or more observers while the patient is voiding. It is obvious that administration of such devices in this manner creates sufficient psychological difficulties for many of the patients to effect voiding. Consequently, if the patients void at all, the potentially erroneous data obtained may result in a false diagnosis and a loss of confidence in the device by the physician. A further complication arises from the fact that many of these devices are rather bulky, and somewhat difficult to use.

SUMMARY OF THE INVENTION

A principal feature of the present invention is the provision of a device for measuring a discharge of liquid of simplified construction, and which may be self-administered by a patient.

The device of the present invention comprises, a hollow receptacle having inlet port means adjacent an upper end of the receptacle to receive the liquid discharge and channel means communicating with the inlet port means to receive the liquid passing through the port means, and means for directing at least a portion of the discharge from the port means to a predetermined location in the channel means. The device has means for diverting a portion of the discharge from the predetermined location in the channel means to a second location outside the channel means, and means for limiting passage of liquid along the diverting means. The device also has cavity means for receiving the diverted portion of the discharge at the second location outside the channel means, a collection chamber below the cavity means to receive liquid from the cavity means, means for limiting passage of liquid from the cavity means to the chamber, and means for directing overflow of liquid from the cavity means to the channel means below the diverting means. The device may also have means for determining the approximate peak flow rate of the discharge passing through the channel means, and means for determining the approximate volume of liquid passing through the channel means.

A feature of the present invention is that the duration of time for the liquid discharge may be determined by the height of liquid collected in the collection chamber.

Another feature of the present invention is that the approximate peak flow rate and volume of the liquid discharge may be determined by the device.

Yet another feature of the invention is that the average flow rate of the liquid discharge may be determined by the height of liquid collected in the chamber which indicates voiding time and the total volume of liquid collected by the device.

Still another feature of the invention is that the time measuring portion of the device diverts a relatively small portion of the discharge, and minimizes the effects on other parameters measured by the device.

A feature of the invention is that the time measuring portion of the device provides a determination of the duration of the discharge with improved accuracy.

A further feature of the invention is that the device measures the duration of the discharge passing into the device even when the discharge has a relatively low volumetric flow rate.

Further features will become more fully apparent in the following description of the embodiments of this invention and from the appended claims.

DESCRIPTION OF THE DRAWINGS

In the drawings:

FIG. 1 is a fragmentary perspective view of a liquid measuring device of the present invention;

FIG. 2 is a perspective view, partly broken away, of the device of FIG. 1 illustrating a time measuring portion of the device;

FIG. 3 is a top plan view of the device of FIG. 1;

FIG. 4 is an elevational view, taken partly in section, of the device of FIG. 1;

FIG. 5 is a fragmentary sectional view taken substantially as indicated along the line 5—5 of FIG. 1;

FIG. 6 is a fragmentary sectional view taken substantially as indicated along the line 6—6 of FIG. 1; and FIG. 7 is an exploded view, taken partly in section, of a time measuring portion of the device of FIG. 1.

DESCRIPTION OF THE PREFERRED EMBODIMENTS

Referring now to FIGS. 1-4, there is shown a device generally designated 20 for measuring and collecting a discharge of liquid, such as urine. The device 20 includes a hollow receptacle designated generally 22 having a cavity 23, and a container designated generally 24 having an upper end 25 releasably attached to a lower end 27 of the receptacle 22. Preferably, the receptacle 22 is made from a suitable transparent material, such as plastic.

The receptacle 22, which has rounded end portions and an elongated central portion, has an upright wall 26 which extends laterally across the inside of the receptacle and which extends vertically substantially the height of the receptacle. The upright wall 26 separates the inside of the receptacle into a compartment 28 and a passageway or channel 30. The lower end of the compartment 28 is closed by a bottom wall 31, while the upper end of the passageway 30 and compartment 28 is partially covered by an upper wall 32.

The receptacle 22 has an enlarged portion 34 adjacent the upper end of the receptacle defining an inlet port or opening means 36 to receive the incoming urine discharge, as indicated by the direction of the arrows in FIG. 1. The receptacle has a wall 38 extending laterally across the inside of the receptacle, and having a lower end 40 defining a space 42 intermediate the lower end 40 of the wall 38 and the lower or the bottom wall 31 of the receptacle. The wall 38 partially defines the compartment 28 and a channel or channel means 44 intermediate the wall 38 and an outer side wall 45 of the receptacle 22. Thus, a major portion of the urine discharge passes from the opening means 36 through the channel means 44 and space 42 into the compartment 28.

The wall 26 has an elongated vertical slot or opening means 46 communicating between the compartment 28 and the passageway means 30 to permit passage of the liquid from the compartment to the passageway means and into a chamber 52 in the container 24. As shown in FIGS. 1 and 4, an indicating strip 54 is removably inserted into the compartment 28, with retaining means 56 adjacent the lower end 27 of the receptacle releasably receiving a lower end of the indicating strip 54. As shown in FIG. 1, the retaining means 56 has a pair of bosses extending from the bottom wall 31 into the cavity 23, with the bosses defining a slot which receives the lower end of the strip 54 and assists in retaining the strip 54 in an upright position in the compartment 28.

As shown in FIG. 4, a retaining member 62 has an elongated flexible tab 64 having first and second spaced plugs 66 and 68, respectively, extending outwardly from one surface of the tab 64, with the first plug 66 being located adjacent one end of the tab 64, and the other plug 68 being located intermediate the plug 66 and the other end of the tab. The first plug 66 has a slot to receive and retain an upper end of the indicating strip 54. The upper wall 32 has a first opening communicating with the compartment 28 to receive the indicating strip 54 and first plug 66, with the first opening having dimensions to snugly engage the first plug 66. The upper wall 32 also has a second opening extending through the wall to snugly receive the second plug 68. Thus, the first and second plugs 66 and 68 are removably received in the first and second openings to releasably retain the tab 64 in place above the upper wall 32, while the first plug 66 assists in retaining the upper end of the indicating strip 54 in an upright position in the compartment 28. As shown in FIGS. 1 and 4, the outer end of the tab 64 extends past the enlarged portion 34 to facilitate removal of the retaining member 62 from the receptacle 22.

The indicating strip 54 is sensitive to contact or wetting by liquid, such as urine, and provides an indication of the maximum height of liquid reached in the compartment 28 during the liquid discharge. Any suitable material may be utilized for the indicating strip 54, such as a material which changes color upon contact by the liquid. For example, a methylene blue compound or rhodamine may be utilized on the strip 54 to obtain the color contrast desired. Preferably, the indicating strip 54 is utilized a single time to measure the height of liquid in the compartment 28. Thus, the retaining member 62 permits easy placement and removal of indicating strips 54 in the receptacle 22. After removal of the strip, flow rate information may be determined by suitable indicia I' spaced along the strip. If desired, the strip 54 may be discarded after it has been removed and the information determined. Alternatively, if it is desired to keep the strip for a later reading, the other end of the tab 64 may be placed in a clip (not shown), or the second plug 68 may be positioned in an opening of a retaining device (not shown) to retain the strip until it is read. In either event, the retaining member 62 permits handling of the strip 54 in a sanitary manner without contacting the strip with the user's hands.

As shown in FIGS. 1 and 4, the container 24 has an upper resilient support member 78 which is releasably attached to a flange 80 at the lower end 27 of the receptacle 22. The support member 78 also includes a closure plug 82 attached to the support member 78 by a strap 84. The plug 82 is removably received in an opening of the support member 78 when the container 24 is removed from the receptacle 22. As shown, the container 24 has a pair of flexible side walls depending from the support member 78 and defining the chamber 52. The container side walls may be made of any suitable material, preferably transparent, such as polyethylene, and one of the side walls may have a plurality of vertically spaced indicia to measure the volume of liquid collected in the chamber 52.

With reference to FIGS. 1-4, the device 20 has a time device generally designated 90 secured to the receptacle 22 over an opening 92 in the side wall 45 of the receptacle 22. The time device 90 has an elbow member 94 having peripheral flanges 96 which may be secured to the side wall 45 of the receptacle 22 about the receptacle opening 92. It will be apparent that the time device 90 may be secured to the receptacle by any suitable means, such as adhesive, or it may be removably attached to the receptacle 22, with the opening 92 of the receptacle 22 being covered by a suitable plate in the event that the time device 90 is removed from the receptacle.

As shown in FIGS. 1-7, the time device 90 has an inclined diverting plate 98 having an upper inner end 100 positioned in the channel 44 of the receptacle 22, and a lower outer end 102 positioned in a compartment 104 defined by the elbow member 94. The inner end 100 of the diverting plate 98 is preferably located centrally laterally across the channel 44, and has a width less than the dimensions of the channel 44. The elbow member 94 has an upright barrier plate 106 extending vertically from the diverting plate 98 and defining an upper inner end of the compartment 104. As shown, the barrier plate 106 has an aperture 108 adjacent the diverting plate 98 to limit passage of liquid along the diverting plate 98 into the compartment 104.

The elbow member 94 has a cylindrical cavity 110 positioned below the outer end 102 of the diverting plate 98 in the compartment 104 in order to receive liquid passing through the aperture 108 along the diverting plate 98. The elbow member 94 also has a return plate 112 extending from an upper end of the cavity 110 to the receptable channel 44 in the opening 92 beneath the diverting plate 98, such that the diverting plate 98 and return plate 112 define an overflow opening 114 to permit passage of overflow liquid from the cavity 110 back into the receptacle channel 44 through the overflow opening 114.

The time device 90 also has a container 116 depending from the elbow member 94 and defining a chamber 118 below the collection cavity 110. As shown, the elbow member 94 may have an annular groove 120 to removably receive an upper cylindrical sleeve 122 of the container 116, such that the container 116 may be removably attached to the elbow member 94. The elbow member 94 has a bore 124 at the lower end of the cavity 110 and communicating between the cavity 110 and chamber 118 when the container 116 is attached to the elbow member 94. As will be seen below, the bore 124 of the elbow member 94 limits the passage of liquid from the cavity 110 to the chamber 118 during use of the device. The container 116 may have an opening 126 to vent the container chamber 118, and may have a vertical section 128 of reduced dimensions in the vertical region of the container 116 where the expected maximum height of liquid will be collected in the chamber 118 for improved accuracy of the device. In this connection, the transparent container 116 may have vertically disposed indicia I which are precalibrated to indicate the time duration of the liquid discharge in association with the maximum height of liquid collected in the container chamber 118.

With reference to FIGS. 1-4, the receptacle 22 has a directing member 130 secured to the upper wall 32 and extending into an opening 132 at the upper end of the receptacle channel 44. As shown, the directing member 130 has a lower plate 134 and a pair of upwardly directed side flanges 136 which are disposed at an angle in order to define a narrow end portion of a chute 138 located adjacent the receptacle opening 132 above the inner end 100 of the diverting plate 98. In this manner, the member 130 directs at least a portion of the liquid discharge into the central portion of the receptacle channel 44 and onto the inner end 100 of the diverting plate 98. Further, the directing member 130 ascertains that at least a portion of the incoming discharge will reach the diverting plate 98 in the event of a relatively low volumetric flow rate of urine discharge.

In use of the device, the plug 82 of the container 24 is removed from the opening of the support member 78, and the support member 78 of the container 24 is attached to the lower end 27 of the receptacle 22. The port 36 of the receptacle 22 is then positioned by a patient in privacy to receive the discharge of urine. As the liquid discharge passes into the enlarged portion 34 of the receptacle 22, the enlarged portion directs the discharge toward the opening 132 at the upper end of the receptacle channel 44. In turn, as the discharge passes into the channel 44 of the receptacle 22, the directing member 130 directs at least a portion of the discharge against the diverting plate 98 of the time device 90. Thus, a portion of the discharge may pass by the sides of the diverting plate 98 in the channel 44, while the remaining portion of the discharge is directed against the diverting plate 98. A minor portion of the discharge then passes along the diverting plate 98 through the aperture 108 of the barrier plate 106 and into the compartment 104 of the elbow member 94, while a major portion of the discharge striking the diverting plate 98 passes around the diverting plate 98 and into a lower portion of the receptacle channel 44. In this manner, the time device 90 limits the quantity of liquid discharge passing into the compartment 104 in order to minimize the effect which diverted liquid might otherwise have upon a determination of peak flow rate and volume of the discharge, as described below. Moreover, the barrier plate aperture 108 limits the force of impact the liquid may have upon the head of liquid which accumulates in the collection cavity 110.

Thus, the limited amount of liquid passing along the diverting plate 98 flows into the cavity 110 of the elbow member 94, and collects in the cavity 110 until a sufficient liquid volume or head causes passage of liquid through the bore 124 into the container chamber 118 for collection therein. Accordingly, once a sufficient head of liquid has collected in the cavity 110, the collected liquid passes at a uniform rate through the bore 124 into the chamber 118 during the remainder of the discharge. The liquid thus collects at a uniform rate in the container chamber 118 during the discharge, and the volume of collected liquid in the chamber 118 provides an indication of the duration of the liquid discharge, as determined by the precalibrated indicia I on the container 116. In the event that the diverted portion of the discharge accumulates to a level above the cavity 110 of the elbow member 94, the excessive portion of the accumulated liquid passes along the return plate 112 through the overflow opening 114 back into the receptacle channel 44 for subsequent passage into a lower part of the receptacle 22. In this manner, a minor portion of the incoming liquid discharge is diverted into the time device 90 in order to determine the time duration of the liquid discharge while an excessive portion of the discharge is returned to the receptacle 22.

As previously discussed, a major portion of the incoming liquid discharge passes around the diverting plate 98 of the time device into a lower part of the receptacle channel 44, while an excess of the liquid from the time device 90 is returned through the overflow opening 144 into the channel 44. Thus, a major portion of the liquid passes through the channel 44, collects in the lower part of the compartment 28, and then passes from the compartment 28 through the slot 46 into the passageway 30. From the passageway, the liquid flows into the chamber 52 of the container 24 for collection therein. As the rate of discharge into the receptacle increases, the height of liquid in the compartment 28 also increases while the liquid also drains through the slot 46 into the passageway 30.

For a given rate of flow of the discharge into the receptacle the liquid attains a fixed height in the compartment 28, and the liquid passes at a fixed rate of flow through the slot 46. Hence, if the rate of flow of the liquid discharge into the receptacle increases, the height of liquid in the compartment raises an additional amount, and the rate of flow through the slot 46 also increases, since the liquid flows through a larger vertical portion of the slot 46. Thus, as long as the rate of flow of the discharge into the receptacle increases, the height of liquid in the compartment 28 continues to rise, and the rate of flow of liquid through the slot 46 also increases. When the flow rate of the incoming discharge abates, the liquid drains from the compartment 28 into the passageway 30 faster than it enters the compartment, and the height of the liquid in the compartment begins to subside.

Peak flow rate of the incoming liquid discharge may be defined as the maximum rate of flow of the discharge. Since the height of liquid in the compartment raises or lowers responsive to an increase or decrease, respectively, of the flow rate of the incoming discharge, it is apparent that the maximum height of liquid attained in the compartment during the discharge serves as an indication of the approximate peak flow rate of the discharge. Although anomalies in the discharge, such as a momentary surge of the discharge, may not be ultimately reflected in the maximum liquid height in the compartment, due, in part to the lag between the time the discharge enters the receptacle and the time it enters the compartment, the device determines the peak flow rate with sufficient accuracy for such purposes as are under discussion. In particular, a urine stream during voiding has a relatively slow rate of change of flow rate, and the device of the present invention indicates a peak flow rate for the discharge which is sufficiently accurate for purposes of diagnosing the patient.

It is possible that the approximate peak flow rate of the urine discharge may be determined by observing the highest level of liquid accumulated in the compartment 28 during the discharge. Direct reading by the patient may be impractical of difficult during self-administration of the apparatus as thus far described, if the apparatus is utilized to collect a discharge of liquid during voiding, and it is desirable that the device be self-administered by the patient in order to alleviate any psychological problems of the patient which might be caused by observation of the receptacle during voiding.

Accordingly, the indicating strip 54 has been provided to automatically record the approximate maximum height of liquid collected in the compartment 28 during the liquid discharge. After the liquid discharge has been completed, a direct reading of the approximate peak flow rate may be determined by the indicia I′, either before or after removal of the indicating strip 54 from the receptacle 22. Alternatively, the indicia I′ may be placed on the wall of a transparent receptacle 22.

It is apparent that the rate of drainage from the compartment 28 into the passageway 30 is partly dependent upon the precise structure of the receptacle 22. For example, although the slot 46 is shown as having parallel sides, it is contemplated that the slot may be widened or narrowed at desired vertical positions to increase or decrease the flow rate of liquid through the wall in that area, and the wall 26 may have a plurality of slots or openings if desired. Also, the cross sectional area of the compartment 28 itself may be selected of a suitable size to provide the desired sensitivity of liquid column height for a more accurate determination of the peak flow rate.

It is contemplated that a particular structure for the receptacle would first be established, dependent on the accuracy desired and the expected range of values for the peak flow rate of the liquid discharge. Next, the receptacle could be calibrated against known constant flow rates of a discharge passing into the receptacle to determine the appropriate location of the indicia I′ on the strip. That this may be readily accomplished is apparent from the fact that the peak flow rate for a discharge having a constant flow rate is the value of the constant flow rate itself. Accordingly, when the discharge of constant flow rate is directed into the receptacle, liquid rises in the compartment to a level at which liquid entering the compartment is offset by the liquid draining from the compartment into the channel, and the receptacle or strip is marked at this height for peak flow rate by the value of the flow rate of the constant discharge.

As noted above, once the rate of flow of the liquid discharge into the receptacle abates, the height of the liquid in the compartment 28 subsides, and the approximate peak flow rate has already been determined on the indicating means or strip 54. During the remainder of the liquid discharge, the liquid continues to drain from the compartment 28 into the passageway 30 until the discharge is terminated and drainage from the compartment to the channel eventually stops. Since the liquid drains from the passageway 30 of the receptacle 22 into the container 24, the volume of liquid which collects in the container 24 during the liquid discharge may be readily determined by the indicia on the container 24.

Since the patient may use the device without observation, unnatural voiding or failure to void which normally occur from psychological difficulties when a patient voids under observation is prevented. After voiding, the patient merely summons the physician or nurse, who then uses the device to diagnose the patient's voiding. As previously indicated, the indicating strip 54 may be removed from the receptacle to obtain a reading of the peak flow rate of the urine discharge by use of the indicia I′ on the strip 54, or the strip may be retained for later use if desired. The container 24 may be removed from the receptacle 22 to obtain a specimen of urine from the chamber 52 of the container 24 through the container opening. Alternatively, the closure plug 82 may be placed in the container opening to close the opening and cavity 52 of the container 24, and the specimen may be retained for later use, if desired. In either event the closed container 24 may be discarded in a sanitary manner after removal from the receptacle 22. The receptacle 22 may be cleaned and sterilized for future use with a different indicating strip 54, to reduce the cost of diagnosing various patients.

Thus, the time duration of the discharge may be readily determined by the indicia I on the container 116 of the time device 90 by comparing the height of liquid collected in the container chamber 118 during the discharge against the indicia I, and the peak flow rate of the discharge may be readily determined by the indicating strip 54. Further, the total volume of the discharge collected in the chamber 52 of the container 24 less the volume of liquid collected in the container chamber 118 may be readily determined through the use of suitable indicia on the side walls of the container 24. Of course, the volume of liquid collected in both chambers 52 and 118 may be calculated through use of suitable volume indicia on the container 116 and the volume indicia of receptacle 24 in order to define a precise total volume on the collected discharge, if desired. Accordingly, the total volume value of the discharge may be divided by the time duration value of the discharge in order to provide the physician with an average flow rate value of the discharge. Moreover, if desired, the container 116 of the time device 90 may be removed from the elbow member 94 in order to provide a convenient specimen of the discharge.

The foregoing detailed description is given for clearness of understanding only, and no unnecessary limitations should be understood therefrom, as modifications will be obvious to those skilled in the art.

I claim:

1. A device for measuring a liquid discharge, comprising: a hollow receptacle having an inlet port adjacent an upper end of the receptacle to receive the liquid discharge and channel means communicating with the inlet port to receive the liquid passing through the inlet port, means for diverting only a portion of the discharge from the channel means while permitting passage of an additional portion of the discharge through the channel means, cavity means to receive the diverted portion of the discharge from the diverting means, a collection chamber below the cavity means to receive liquid from the cavity means, and means for limiting passage of liquid from the cavity means into the collection chamber, said additional portion of the discharge passing through the channel means without passing into the cavity means.

2. The device of claim 1 including means for limiting passage of liquid from the channel means through the diverting means.

3. The device of claim 1 including means for directing overflow of liquid from the cavity means into the channel means.

4. The device of claim 1 including means for directing at least a portion of the discharge passing through the inlet port toward the diverting means.

5. The device of claim 1 including means for determining the approximate peak flow rate of the discharge passing through the channel means.

6. The device of claim 1 including means for determining the approximate volume of liquid passing through the channel means.

7. The device of claim 1 wherein said collection chamber has a reduced cross-sectional area in the vertical region of expected liquid to be collected.

8. The device of claim 1 wherein said collection chamber has associated vertically disposed indicia.

9. The device of claim 1 including means for venting said chamber.

10. A device for measuring a liquid discharge, comprising: a hollow receptacle having inlet port means adjacent an upper end of the receptacle to receive the liquid discharge, channel means below the inlet port means to receive the liquid passing through the port means, and means for directing at least a portion of the discharge from the port means to a predetermined location in the channel means, said device including means for diverting only a portion of the discharge from said predetermined location in the channel means, means for limiting passage of the diverted liquid along the diverting means and for excluding a portion of the diverted liquid, cavity means for receiving the limited portion of the diverted discharge at a second location outside the channel means while said excluded portion passes into the channel means without passing into the cavity means, a container defining a collection chamber below the cavity means to receive liquid from the cavity means, means for limiting passage of liquid from the cavity means to the chamber, and means for directing overflow of liquid from the cavity means to the channel means below the diverting means.

11. The device of claim 10 including means for releasably attaching said container to the device.

12. A device for measuring a liquid discharge, comprising: a hollow receptacle having inlet port means adjacent an upper end of the receptacle to receive the liquid discharge, and a wall at least partially defining channel means below the inlet port means to receive the liquid passing through the port means, said device having an inclined diverting plate extending through an opening in said wall and having an upper inner end positioned in the channel means and a lower outer end located outside said wall relative the channel means, with said inner end of the diverting plate having a width less than the inner dimensions of the channel means, a barrier member extending above the diverting plate adjacent said wall and having an opening adjacent the diverting plate to limit passage of liquid along the diverting plate, a cavity positioned below the outer end of the diverting plate to receive liquid from the diverting plate, a collection chamber below said cavity to receive liquid from the cavity, a bore communicating between said cavity and chamber to limit the passage of liquid between the cavity and chamber, and an overflow plate extending between an upper end of said cavity to said channel means below the diverting plate in the wall opening to define an aperture intermediate the diverting and overflow plates for passage of overflow liquid from the cavity to channel means.

13. The device of claim 12 wherein said receptacle includes an upper wall and back wall defining said port means and opening means communicating between the port means and channel means, and including means for directing a portion of the incoming discharge from the port means through the opening means onto the inner end of the diverting plate comprising, a directing member having a pair of upright side flanges adjacent an inner portion of the upper wall and defining a chute to direct the liquid toward the diverting plate.

14. A device for measuring the duration of a liquid discharge, comprising: a housing having a liquid receiving compartment, means for diverting only a portion of the discharge into said compartment, first means for limiting passage of liquid through the diverting means, a cavity to receive the diverted liquid from the diverting means in said compartment, a chamber to receive liquid from the cavity, second means for limiting passage of liquid from the cavity to chamber, means for directing overflow of liquid from the cavity out of the compartment, and channel means for directing a remaining portion of the discharge around the diverting means and from the first limiting means without passing into the compartment.

* * * * *